(12) United States Patent
Okita et al.

(10) Patent No.: US 9,382,169 B2
(45) Date of Patent: Jul. 5, 2016

(54) LOWER OLEFINS PRODUCING CATALYST AND METHOD FOR PRODUCING LOWER OLEFINS USING SAME

(75) Inventors: Atsushi Okita, Higashiibaraki-gun (JP); Kazunori Honda, Higashiibaraki-gun (JP); Chizu Inaki, Higashiibaraki-gun (JP); Jumpei Takahashi, Higashiibaraki-gun (JP); Masashi Yamaguchi, Yokohama (JP); Yumiko Yoshikawa, Yokohama (JP); Shinji Iwade, Kurashiki (JP); Tohru Setoyama, Yokohama (JP)

(73) Assignees: JGC CORPORATION, Tokyo (JP); MITSUBISHI CHEMICAL CORPORATION, Tokyo (JP)

( * ) Notice: Subject to any disclaimer, the term of this patent is extended or adjusted under 35 U.S.C. 154(b) by 1221 days.

(21) Appl. No.: 13/333,383

(22) Filed: Dec. 21, 2011

(65) Prior Publication Data

US 2012/0116143 A1 May 10, 2012

Related U.S. Application Data

(63) Continuation of application No. PCT/JP2010/060035, filed on Jun. 14, 2010.

(30) Foreign Application Priority Data

Jun. 22, 2009 (JP) ................................. 2009-147805

(51) Int. Cl.
| | |
|---|---|
| B01J 29/06 | (2006.01) |
| C07C 1/20 | (2006.01) |
| B01J 29/40 | (2006.01) |
| B01J 35/02 | (2006.01) |
| B01J 37/00 | (2006.01) |
| B01J 35/00 | (2006.01) |
| B01J 37/02 | (2006.01) |
| B01J 35/04 | (2006.01) |

(52) U.S. Cl.
CPC . *C07C 1/20* (2013.01); *B01J 29/40* (2013.01); *B01J 35/0026* (2013.01); *B01J 35/023* (2013.01); *B01J 37/0009* (2013.01); *B01J 35/026* (2013.01); *B01J 35/04* (2013.01); *B01J 37/0246* (2013.01); *B01J 2229/186* (2013.01); *B01J 2229/42* (2013.01); *C07C 2521/04* (2013.01); *C07C 2521/08* (2013.01); *C07C 2521/16* (2013.01); *C07C 2529/40* (2013.01); *C07C 2529/70* (2013.01); *Y02P 20/52* (2015.11); *Y02P 30/42* (2015.11)

(58) Field of Classification Search
USPC ................... 502/60, 64, 68, 77; 585/639, 640
See application file for complete search history.

(56) References Cited

U.S. PATENT DOCUMENTS

| 4,564,603 | A | * | 1/1986 | Robinson et al. ............... 502/60 |
|---|---|---|---|---|
| 4,801,567 | A | * | 1/1989 | Moorehead ..................... 502/77 |
| 6,046,373 | A | * | 4/2000 | Sun ............................... 585/640 |
| 7,229,941 | B2 | | 6/2007 | Burgfels et al. |
| 7,371,916 | B1 | | 5/2008 | Kalnes et al. |
| 2004/0182748 | A1 | | 9/2004 | Vijayanand et al. |
| 2005/0245780 | A1 | | 11/2005 | Chang et al. |
| 2007/0032379 | A1 | * | 2/2007 | Ito et al. ........................ 502/213 |
| 2008/0146721 | A1 | * | 6/2008 | Kaminsky et al. ............ 524/450 |
| 2010/0168492 | A1 | | 7/2010 | Inaki et al. |

FOREIGN PATENT DOCUMENTS

| CA | 1 165 333 | 4/1984 |
|---|---|---|
| EP | 1 685 897 A2 | 8/2006 |
| JP | 57-197228 | 12/1982 |
| JP | 2004-181454 | 7/2004 |
| JP | 2005-138000 | 6/2005 |
| JP | 2005-314339 | 11/2005 |
| JP | 2007-61674 | 3/2007 |
| JP | 2008-074764 | 4/2008 |
| JP | 2008-080301 | 4/2008 |
| JP | 2008-513448 | 5/2008 |

OTHER PUBLICATIONS

Machine translation of JP 2008-074764, Apr. 2008.*
U.S. Appl. No. 13/361,616, filed Jan. 30, 2012, Yamaguchi, et al.
Extended Search Report issued Apr. 1, 2015 in European Patent Application No. 10791994.6.

* cited by examiner

*Primary Examiner* — Elizabeth Wood
(74) *Attorney, Agent, or Firm* — Oblon, McClelland, Maier & Neustadt, L.L.P.

(57) ABSTRACT

A lower olefin producing catalyst which has high olefin production efficiency and maintains its activity for a long period of time when lower olefins are produced from an oxygen-containing compound, which is a solid catalyst used in producing lower olefins from an oxygen-containing compound, includes a solid-state catalyst component containing an MFI-type zeolite, in which, at a position where the shortest distance to the outer surface is maximum among all positions inside a structure of the solid catalyst, the thickness defined as a distance twice the shortest distance from the point to the outer surface is in a range of from 0.1 to 2.0 mm, and a method for producing lower olefins.

16 Claims, 3 Drawing Sheets

Thickness = d

If D < L, d = D
If D > L, d = L d = R

Columnar

Spherical

LOWER OLEFINS PRODUCING CATALYST AND METHOD FOR PRODUCING LOWER OLEFINS USING SAME

CROSS REFERENCE TO RELATED APPLICATIONS

This application is a continuation application of PCT/JP2010/060035 filed on Jun. 14, 2010, and claims priority to Japanese Patent Application No. 2009-147805 filed on Jun. 22, 2009.

TECHNICAL FIELD

The present invention relates to lower olefins producing catalyst and a method for producing lower olefins using the catalyst. More particularly, the invention relates to a catalyst which is used in producing lower olefins, such as propylene, from oxygen-containing compounds, such as dimethyl ether, and which has high selectivity of lower olefins and good catalyst life, and a method for producing lower olefins using the catalyst.

BACKGROUND ART

Conventionally, lower olefins, such as propylene and ethylene, have been produced from oxygen-containing compounds, such as dimethyl ether and methanol, by dehydrating condensation reactions, in which zeolite catalysts are mainly used. Industrially, it has been desired to produce lower olefins from oxygen-containing compounds, such as dimethyl ether and methanol, economically with higher yield. More efficient processes and highly active catalysts have been required, and various studies have been conducted.

In order to improve the yield of lower olefins, reduction in feedstock partial pressure during reactions is conceivable. As such a method, for example, a technique has been known in which feedstocks are diluted with gas which is inert to reactions (Patent Document 1).

With respect to a technique for catalyst improvement, an alkaline-earth metal-containing MFI-type zeolite catalyst has been proposed as a catalyst giving a high yield of lower hydrocarbons synthesized from dimethyl ether and/or methanol, the alkaline-earth metal-containing MFI-type zeolite catalyst having a Si/Al atomic ratio of 30 to 400, an alkaline-earth metal/Al atomic ratio of 0.75 to 15, and an average particle size of 0.05 to 2 μm (Patent Document 2).

Furthermore, Patent Document 3 proposes a zeolite catalyst composed of a mixture including a proton-type zeolite or an ammonium-type zeolite which has MFI-type structure, an alkaline-earth metal compound, and a specific binder component. It is described that when the zeolite catalyst is used as a catalyst for producing lower hydrocarbons from dimethyl ether and/or methanol, aluminum is not easily detached from the zeolite framework, and the catalyst life is long.

Patent Document 5 proposes a zeolite catalyst shaped a mixture which contains pentacyl-type alminosilicate having a primary particle size of 0.01 to 0.1 μm. It is described that when the zeolite catalyst is used as a catalyst for producing lower olefins from methanol, the catalyst has high selectivity of lower olefins and good catalyst life.

However, an improved technique for producing lower olefins from an oxygen-containing compound more efficiently has been desired. Under these circumstances, the applicant of the present invention has conducted diligent studies, and as a result, has found that in the case where a catalyst is designed to have a specific form and the compacted bulk density (CBD) of the catalyst is specific range, surprisingly, a highly active catalyst can be obtained, a long catalyst life can be obtained even though the reaction conditions are under high temperature and pressure, the stable reactions can be achieved, and lower olefins can be produced efficiently. Thus, the present invention has been completed.

With respect to the technique for producing lower olefins from an oxygen-containing compound, the effect of the form, such as size and shape, of catalysts has not been verified. In catalytic cracking of hydrocarbons, such as hexane, it is described that, by using a zeolite catalyst having a large particle size of 1.2 mm or more, the pressure loss of a catalyst layer can be suppressed (Patent Document 4).

CITATION LIST

[Patent Document]
[Patent Document 1] Japanese Unexamined Patent Application Publication No. S57-197228
[Patent Document 2] Japanese Unexamined Patent Application Publication No. 2005-138000
[Patent Document 3] Japanese Unexamined Patent Application Publication No. 2008-80301
[Patent Document 4] Japanese Unexamined Patent Application Publication No. 2005-314339
[Patent Document 5] Japanese Unexamined Patent Application Publication No. 2004-181454

SUMMARY OF INVENTION

Technical Problem

It is an object of the present invention to provide a lower olefin producing catalyst, which has high efficiency for producing lower olefins and maintains its activity for a long period of time when lower olefins are produced from an oxygen-containing compound, and a method for producing lower olefins.

Solution to Problem

According to the present invention, there is provided a lower olefin producing catalyst which is a solid catalyst used in producing lower olefins from oxygen-containing compounds, the lower olefin producing catalyst including a solid-state catalyst component containing an MFI-type zeolite, and the thickness of the catalyst is in a range of 0.1 to 2.0 mm, where the thickness is defined as a distance twice the shortest distance from the outer surface to a position where the shortest distance to the outer surface is maximum among all positions inside a structure of the solid catalyst, and the compacted bulk density (CBD) of the catalyst is 800 kg/m$^3$ or less.

Preferably, the lower olefin producing catalyst of the present invention is obtained by shaping a mixture including the solid-state catalyst component containing an MFI-type zeolite, and at least one binder selected from the group consisting of oxides or hydroxides of aluminum, oxides or hydroxides of silicon and clay.

Preferably, the lower olefin producing catalyst of the present invention is a catalyst used in producing lower olefins from dimethyl ether and/or methanol.

In the lower olefin producing catalyst of the present invention, preferably, the solid-state catalyst component contains an alkaline-earth metal component, and more preferably, the solid-state catalyst component contains the alkaline-earth metal component of 0.3 to 10 parts by weight in terms of metal relative to 100 parts by weight of the MFI-type zeolite.

In such a lower olefin producing catalyst of the present invention, preferably, the alkaline-earth metal is calcium.

In the lower olefin producing catalyst of the present invention, preferably, the compacted bulk density (CBD) of the catalyst is 800 kg/m$^3$ or less. Preferably, the lower olefin producing catalyst of the present invention is honeycomb-shaped.

In the lower olefin producing catalyst of the present invention, preferably, the atomic ratio Si/Al in the zeolite framework of the MFI-type zeolite is in a range of 10 to 2,000.

According to the present invention, there is provided a method for producing lower olefins producing catalyst which is used in producing lower olefins from an oxygen-containing compound, the method including a step of preparing a mixture by mixing/kneading a solid-state catalyst component containing an MFI-type zeolite and at least one binder selected from the group consisting of oxides or hydroxides of aluminum, oxides or hydroxides of silicon and clay in the presence of a polar solvent; and a step of shaping the mixture and calcining the shaped mixture, to obtain the catalyst having a thickness in a range of 0.1 to 2.0 mm, where the thickness is defined as a distance twice the shortest distance from the outer surface to a position where the shortest distance to the outer surface is maximum among all positions inside a structure of the solid catalyst, and the catalyst having the compacted bulk density (CBD) of 800 kg/m$^3$ or less.

According to the present invention, there is provided a method for producing lower olefins including a step of contacting an oxygen-containing compound with the lower olefin producing catalyst of the present invention in a reactor into which the catalyst has been packed.

According to the present invention, there is provided a method for producing lower olefins including a step of contacting an oxygen-containing compound with the lower olefin producing catalyst of the present invention in a reactor into which the catalyst has been packed at 500° C. to 650° C. of outlet temperature under 0.12 MPa to 1.0 MPa of inlet pressure.

In the method for producing lower olefins according to the resent invention, preferably, the oxygen-containing compound contains dimethyl ether and/or methanol, and preferably, the catalyst packing density in the reactor is 800 kg/m$^3$ or less.

Advantageous Effects of Invention

According to the present invention, it is possible to provide lower olefins producing catalyst which has high catalytic activity and a long catalyst life.

Furthermore, according to the present invention, because the catalyst has long life, the frequency of catalyst regeneration can be decreased, and it is possible to reduce the cost associated with catalyst replacement and regeneration. It is also possible to provide a method for producing lower olefins efficiently in which the amount of the catalyst to be packed can be reduced. Furthermore, according to the present invention, since the catalyst packing density in the reactor can be decreased, the length/diameter ratio of the reactor can be increased.

DESCRIPTION OF EMBODIMENTS

Figure 1:
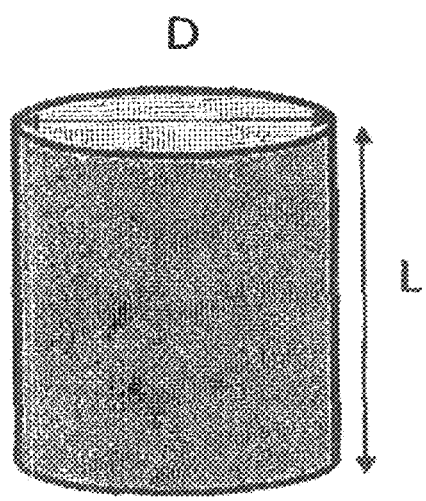
FIG. 1 is a schematic diagram illustrating the thickness of the catalyst in the case where the catalyst shape is columnar and spherical.
Figure 1:
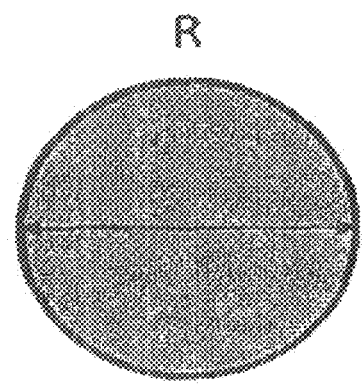

The present invention will be described specifically below.
<Lower Olefins Producing Catalyst>

Lower olefins producing catalyst according to the present invention is a solid catalyst used in producing lower olefins from an oxygen-containing compound and includes a solid-state catalyst component containing an MFI-type zeolite.

As the MFI-type zeolite constituting the lower olefin producing catalyst of the present invention, a proton-type zeolite and/or an ammonium-type zeolite may be used. In the MFI-type zeolite used in the present invention, the Si/Al mole ratio is preferably in a range of 10 to 2,000, and more preferably 50 to 1,000. If the Si/Al mole ratio is less than 10, the number of effective acid sites of the zeolite becomes too large, which may promote carbonaceous deposition on the surface of the catalyst, resulting in a decrease in the catalyst life. If the Si/Al ratio exceeds 2,000, the number of effective acid sites of the zeolite becomes too small, which may decrease the catalytic activity.

The lower olefin producing catalyst of the present invention preferably contains an alkaline-earth metal or compound thereof such as oxides or hydroxides (hereinafter, sometimes referred to "alkaline-earth metal component"). The content of the alkaline-earth metal component in terms of metal is preferably 0.3 to 10 parts by weight, more preferably, about 0.5 to 5 parts by weight relative to 100 parts by weight of the MFI-type zeolite. When the catalyst contains the above range of the alkaline-earth metal component, controlling the catalyst acid properties and suppressing dealuminization can be achieved effectively, which is preferable. On the other hand, when the catalyst contains the alkaline-earth metal component in an amount exceeding 10 parts by weight relative to 100 parts by weight of the MFI-type zeolite, an excessive amount of the alkaline-earth metal component may cause a side reaction. In the present invention, the alkaline-earth metal included in the catalyst is preferably calcium.

In the lower olefin producing catalyst of the present invention, the thickness of the catalyst is in a range of 0.1 to 2.0 mm, and preferably 0.1 to 1.8 mm, where the thickness is defined as a distance twice the shortest distance from the outer surface to a position where the shortest distance to the outer surface is maximum among all positions inside a structure of the solid catalyst.

In the present invention, as long as the solid catalyst has a thickness satisfying the range described above, the shape of the solid catalyst is not particularly limited. For example, the solid catalyst may be in any shape, such as spherical, prismatic, columnar, circular tubular, ring-shaped, rectangular tubular, cylindrical, wheel-shaped, disc-shaped, rectangular plate-shaped, corrugated, a structure having surface irregularities, honeycomb-shaped, three-leaf-shaped in cross-section, or four-leaf-shaped in cross-section. Among them, bulky shapes are suitable. A four-leaf-shape is particularly preferable. For example, a structure having a space inside or a hollow shape is preferable, and a honeycomb shape is preferable.

As described above, the thickness of the catalyst is in a range of 0.1 to 2.0 mm, and preferably 0.1 to 1.8 mm, where the thickness is defined as a distance twice the shortest distance from the outer surface to a position where the shortest distance to the outer surface is maximum among all positions inside a structure of the solid catalyst. Specifically, for example, the thickness d is determined as follows:

In the case of a columnar structure with a circle diameter D and a length L (refer to FIG. 1), if D<L, the thickness d corresponds to D; and if D>L, the thickness d corresponds to L.

In the case of a spherical structure with a sphere diameter R (refer to FIG. 1), the thickness d corresponds to R.

In the case of a ring-shaped structure having concentric inner and outer circumferences in which the delta between the outer diameter and the inner diameter is T and the length is L (refer to FIG. 2), if T<L, the thickness d corresponds to T; and if T>L, the thickness d corresponds to L.

The case of a honeycomb-shaped structure having prismatic hollow spaces extending in the height direction inside is as follows. At the position where the shortest distance to hollow surface or outer surface is maximum among all positions inside, shortest distance between one hollow space and another hollow space is T and the height is L (refer to FIG. 2). If T<L, the thickness d corresponds to T whereas if L<T, the thickness d corresponds to L.

In the case of a rectangular parallelepiped structure, the thickness d corresponds to the length of the shortest side.

In the case of a four-leaf-shaped structure with a length L, outer diameter D between diagonal leafs, and T defined as a length between diagonal depressions (refer to FIG. 2), if T<L, the thickness d corresponds to T; and if T>L, the thickness d corresponds to L.

In the lower olefin producing catalyst of the present invention, the compacted bulk density (CBD) of the catalyst is usually 800 kg/m$^3$ or less, preferably 700 kg/m$^3$ or less, more preferably 650 kg/m$^3$ or less, and further preferably in a range of 200 to 650 kg/m$^3$. When such a lower olefin producing catalyst is used, the catalyst packing density in the reactor is usually 800 kg/m$^3$ or less, preferably 700 kg/m$^3$ or less, more preferably 670 kg/m$^3$ or less, further more preferably 650 kg/m$^3$ or less and particularly preferably 200 to 650 kg/m$^3$. In the present invention, the term "CBD" means to a bulk density measured by a method, in which a sample is dispersed and placed in a vessel, the vessel is impacted by tapping, and measurement is performed when no change occurs in the volume of the sample.

When the lower olefin producing catalyst of the present invention has a low CBD of 800 kg/m$^3$ or less, it is easy to decrease the catalyst packing density when the catalyst is packed in the reactor, and the pressure loss in the reactor is easily reduced. Thus, a low pressure loss type catalyst can be obtained. By using the low pressure loss type catalyst for producing lower olefins, the reactor can be downsized. Thus, the reactor can be easily designed produced the producing cost of the reactor is reduced.

The CBD of the lower olefin producing catalyst can be easily controlled by selecting the shape of catalyst.

The catalyst has low CBD of 800 kg/m$^3$ or less is a thin catalyst having an uncomplicated general shape.

If the CBD is less than 200 kg/m$^3$, the size of the reactor may be too large and the lower olefin producing cost may be increased.

The lower olefin producing catalyst of the present invention having the thickness described above may be directly produced from a precursor of the MFI-type zeolite, or may be produced by shaping the MFI-type zeolite in the form of powder or the like, if necessary, together with a binder, a solvent, etc.

The lower olefin producing catalyst according to the present invention is preferably produced by preparing a mixture including a solid-state catalyst component containing an MFI-type zeolite and a binder, and shaping the mixture. When the lower olefin producing catalyst of the present invention contains an alkaline-earth metal component, the alkaline-earth metal component may be contained in the solid-state catalyst component, or the alkaline-earth metal component may be added together with the binder. Preferably, the alkaline-earth metal component is contained in the solid-state catalyst component.

The solid-state catalyst component containing the alkaline-earth metal component may be produced by mixing an alkaline-earch metal or a compound thereof with a precursor of the MFI-type zeolite, followed by calcination, or may be produced by impregnating or mixing an alkaline-earth metal or a compound thereof with the MFI-type zeolite.

Examples of the compound of an alkaline-earth metal used in the production of the lower olefin producing catalyst of the present invention include magnesium carbonate ($MgCO_3$), magnesium hydroxide ($Mg(OH)_2$), magnesium oxide (MgO), magnesium acetate (($CH_3COO)_2Mg$), magnesium nitrate ($Mg(NO_3)_2$), magnesium aluminate ($MgAl_2O_4$), magnesium orthosilicate ($Mg_2SiO_4$), calcium carbonate ($CaCO_3$), calcium hydroxide ($Ca(OH)_2$), calcium oxide (CaO), calcium acetate (($CH_3COO)_2Ca$), calcium nitrate ($Ca(NO_3)_2$), calcium aluminate ($CaAl_2O_4$), calcium orthosilicate ($Ca_2SiO_4$), strontium carbonate ($SrCO_3$), strontium hydroxide ($Sr(OH)_2$), strontium oxide (SrO), strontium acetate (($CH_3COO)_2Sr$), strontium nitrate ($Sr(NO_3)_2$), strontium aluminate ($SrAl_2O_4$), strontium silicate, barium carbonate ($BaCO_3$), barium hydroxide ($Ba(OH)_2$), barium oxide (BaO), barium acetate (($CH_3COO)_2Ba$), barium nitrate ($Ba(NO_3)_2$), barium aluminate ($BaAl_2O_4$), and barium silicate. Among these compounds, calcium compounds are preferable in the present invention. Specifically, calcium carbonate ($CaCO_3$), calcium hydroxide ($Ca(OH)_2$), calcium oxide (CaO), calcium acetate (($CH_3COO)_2Ca$), calcium nitrate ($Ca(NO_3)_2$), calcium aluminate ($CaAl_2O_4$), calcium orthosilicate ($Ca_2SiO_4$), or the like is used.

In order to produce a solid-state catalyst component containing an alkaline-earth metal component is produced by mixing the alkaline-earth metal or compound thereof with a precursor of the MFI-type zeolite, followed by calcination, specifically, for example, the production may be performed in the following manner. First, a raw material liquid for zeolite containing 100 parts by mole of a $SiO_2$ source, 0.2 to 4.0 parts by mole of a metal oxide source, 2 to 1,000 parts by mole of an alkali metal ion source, and 2 to 200 parts by mole a structure-directing agent is dissolved in water, and 0.1 to 60 parts by mole of an alkaline-earth metal salt and zeolite seed crystals, in an amount corresponding to 1 to 60% by mass of zeolite generated in the case where synthesis is performed without adding seed crystals, are added thereinto, followed by stirring. In this mixing step, the mixture containing the raw material liquid for zeolite, the alkaline-earth metal salt, and the zeolite seed crystals is formed into an aqueous gel mixture.

Next, the aqueous gel mixture is placed in a vessel, and hydrothermal synthesis is performed by heating and stirring at 60° C. to 250° C. for 1 to 200 hours under self pressure. The reaction product from the hydrothermal synthesis is separated by filtration or centrifugation, washed with water, and then dried, followed by calcination at 300° C. to 700° C. for 1 to 100 hours. By undergoing these steps, a solid-state catalyst component, which is an MFI-type zeolite containing an alkaline-earth metal component, is prepared.

When the MFI-type zeolite containing an alkaline-earth metal component is converted into a proton-type zeolite, after the drying/calcining step described above, a step of subjecting the reaction product to acid treatment or a step of converting the reaction product by ion exchange to an ammonium-type zeolite and another drying/calcining step are further carried out. In the acid treatment, an inorganic acid, such as hydrochloric acid, sulfuric acid, or nitric acid, or an organic acid, such as formic acid or acetic acid, is used. Among them, hydrochloric acid is preferable. Furthermore, ion exchange to the ammonium-type can be performed in an aqueous ammonium salt solution, such as aqueous ammonium, ammonium chloride, ammonium nitrate, or ammonium sulfate.

The lower olefin producing catalyst according to the present invention has a shape having the thickness described above. Such a catalyst shape may be formed when the MFI-type zeolite is produced, or shaping may be performed using a solid-state catalyst component containing an MFI-type zeolite in the form of powder or the like.

When a catalyst with a desired shape is produced using a solid-state catalyst component in the form of powder, a method may be used in which a mixture including the solid-state catalyst component and a binder is prepared, and the mixture is shaped. When the lower olefin producing catalyst contains an alkaline-earth metal component, the alkaline-earth metal or a compound thereof may be contained into the solid-state catalyst component or may be used together with a binder. In any case, the amount of the alkaline-earth metal or a compound thereof, in terms of alkaline-earth metal, is preferably 0.3 to 10 parts by weight, and more preferably about 0.5 to 5 parts by weight, relative to 100 parts by weight of the MFI-type zeolite.

As the binder, at least one binder selected from the group consisting of oxides or hydroxides of aluminum, oxides or hydroxides of silicon and clay is preferably used. The amount of the binder used is not particularly limited, but is 200 parts by weight or less, preferably in a range of 10 to 50 parts by weight, and more preferably in a range of 15 to 30 parts by weight, relative to 100 parts by weight of the solid-state catalyst component.

When a mixture including the solid-state catalyst component and the binder is prepared, a solvent is usually used. As the solvent, a polar solvent is preferable. Examples of the polar solvent that can be used include water and organic polar solvents, such as alcohols (e.g., methanol, ethanol, and propanol), ethers (e.g., diethyl ether and tetrahydrofuran), esters, nitriles, amides, and sulfoxides. Among these polar solvents, water is preferable. Furthermore, when the mixture is prepared, in addition to the polar solvent, an organic acid, such as acetic acid, ammonia water, or the like, which is removed during drying and calcining, may also be used. The amount of the polar solvent used is not particularly limited as long as the resulting mixture has formability. Usually, the polar solvent can be used in an amount of 10 to 150 parts by weight relative to 100 parts by weight of the total of the components other than the polar solvent.

By mixing the components and as necessary, by kneading, a mixture can be prepared. Then, the resulting mixture is formed into a predetermined shape to obtain a shaped body. Examples of the shaping method include extrusion molding using an extruder and spheronization using a spheronizer. In the present invention, in the shaping stage, preferably, a desired catalyst shape with a thickness of 0.1 to 2.0 mm is formed. Alternatively, a method may be used in which a shape with a thickness exceeding 2.0 mm is formed, and after drying or calcining, a shape with a thickness of 0.1 to 2.0 mm is formed by cutting or pulverization The catalyst having a thickness of 0.1 to 2.0 mm can be also produced by applying a slurry containing the solid-state catalyst component to a base material having honeycomb-shaped structure by dip method, coat method, or the like.

The resulting shaped body is, as necessary, dried, and then calcined. Thereby, lower olefins producing catalyst can be obtained. The shaped body may be dried, for example, at 80° C. to 150° C. for 0.5 to 30 hours. The shaped body which has been dried as necessary may be calcined, for example, at 350° C. to 750° C. for 1 to 50 hours.

The lower olefin producing catalyst according to the present invention is a solid catalyst used in producing lower olefins from an oxygen-containing compound, and preferably is used in producing lower olefins from dimethyl ether and/or methanol.

<Method for Producing Lower Olefins>

In a method for producing lower olefins according to the present invention, the lower olefin producing catalyst of the present invention described above is used. That is, in the present invention, lower olefins can be produced by contacting an oxygen-containing compound, which is a feedstock, with the lower olefin producing catalyst of the present invention in a reactor in which the catalyst is packed. The catalytic reaction method includes a fixed-bed reaction method, a fluidized-bed reaction method, or the like.

Examples of the oxygen-containing compound used as the feedstock include alcohols and ethers having 1 to 10 carbon atoms, such as dimethyl ether, methanol, diethyl ether, ethanol, propanol, and butanol; dimethyl carbonate; formaldehyde; and acetone. In particular, dimethyl ether and/or methanol is preferably used.

Temperature/pressure conditions for the reaction are not particularly limited. For example, when a gas containing dimethyl ether and/or methanol is used as a feedstock, the reaction temperature is preferably in a range of 300° C. to 750° C., and more preferably 400° C. to 650° C. The reason for this is that at a temperature lower than 300° C., although advantageous in terms of energy, the catalytic activity is insufficient. On the other hand, at a temperature exceeding 750° C., the coking rate onto the catalyst is high, deactivation rate of the catalyst is fast, and alteration (structural disorder or the like) of the catalyst occurs. Dimethyl ether and/or methanol as a feedstock can be supplied onto the catalyst by diluting with water vapor, a saturated hydrocarbon gas, inert gas, or the like. When the reaction is carried out continuously in a fixed-bed reactor, the weight hourly space velocity (hereinafter, referred to as "WHSV") is preferably 0.025 to 50 g-DME/(g-catalyst·hour). Where the WHSV is the mass of the feedstock supplied in terms of dimetyl ether (hereinafter, referred to as "DME"), per unit catalyst mass and per unit time.

If the WHSV is less than 0.025 g-DME/(g-catalyst·hour), productivity per unit volume of reactor may be low, which is uneconomical. If the WHSV exceeds 50 g-DME/(g-catalyst·hour), it may be impossible to obtain a sufficient catalyst life or catalytic activity. Furthermore, the reaction product on the catalyst can be separated by known separation and refining techniques.

In the production of lower olefins, outlet temperature condition for the reaction is preferably 500 to 600° C. and inlet pressure condition for the reaction is preferably 0.12 to 1.0 MPa. By setting the outlet temperature condition in such a range, it is possible to synthesize lower olefins at high yield. And by setting the inlet pressure condition in such a range, it is possible to synthesize lower olefins at high speed.

In the present invention, the packing density of the lower olefin producing catalyst in a reactor is usually 800 kg/m³ or less, preferably 700 kg/m³ or less, more preferably 670 kg/m³ or less, further more preferably 650 kg/m³ or less, and particularly preferably 200 to 650 kg/m³. By setting the catalyst packing density in such a range, the pressure loss in the reactor is easily reduced, and the reactor running under low pressure can be designed. Even in a commercial plant in which the amount of feedstock supplied is large, reactions can be carried out at low pressure loss without decreasing the thickness of the catalyst layer. Consequently, it is possible to avoid problems, such as dispersion of feedstock gas, caused in the case where a flat reactor with small length/diameter ratio is used as the thickness of the catalyst layer is decreased.

In the present invention, as a catalyst, the lower olefin producing catalyst of the present invention described above is used, in which, at a position where the shortest distance to the outer surface is maximum among all positions inside the structure of the solid catalyst, the thickness defined as a distance twice the shortest distance from the position to the outer surface is in a range of 0.1 to 2.0 mm, and preferably 0.1 to 1.8 mm. By using the lower olefin producing catalyst in which the thickness of the solid catalyst is 0.1 mm or more, the catalyst can have strength sufficiently endurable for practical use. Furthermore, by using the lower olefin producing catalyst in which the thickness of the solid catalyst is 2.0 mm or less, it is possible to suppress a decrease in activity owing to carbonaceous deposition. If the thickness of the catalyst exceeds 2.0 mm, although pressure loss may be reduced, carbonaceous deposition on the surface of catalyst may increase, and activity may decrease early. As a result, there may be a case in which a catalyst life commensurate with the amount of catalyst packed cannot be obtained, which may be undesirable.

In the present invention, the reaction apparatus used for reactions is not particularly limited. A reactor may be used alone, or a plurality of reactors may be used in series or in parallel.

In the present invention, by using the lower olefin producing catalyst of the present invention described above, it is possible to synthesize lower olefins from an oxygen-containing compound feedstock at high yield. It is also possible to provide a method for producing lower olefins in which reaction efficiency is improved, time before the catalyst deactivation is long, and the catalyst regeneration cost can be reduced.

In the method for producing lower olefins according to the present invention, in the actual industrial operation, preferably, the oxygen-containing compound introduced as a feedstock gas, for example, dimethyl ether and/or methanol, is not present in the product. The conversion of the reactant is preferably 95% or more, more preferably 99% or more, and further preferably 99.9% or more. The conversion can be determined according to the formula below. In the examples described later, the conversion is determined according to the formula below.

Conversion (%)={(Supply velocity of reactant [mol-C/hr])−(Outlet velocity of reactant [mol-C/hr])}/ (Supply velocity of reactant [mol-C/hr])×100  [Formula 1]

In the above formula, the reactant means the total of oxygen-containing compounds (for example, the total of dimethyl ether and methanol), and the supply velocity and the outlet velocity are velocities in terms of carbon.

In the present invention, lower olefins are desirably produced at such a high conversion of the reactant, and therefore, the point at which a given conversion fails to be achieved can be considered as the catalyst life.

EXAMPLES

The present invention will be described more specifically below on the basis of the examples. However, it is to be understood that the present invention is not limited to the examples.

Example 1

Production of Catalyst A 9.50 g of $Al(NO_3)_3 \cdot 9H_2O$ and 10.92 g of $Ca(CH_3COO)_2 \cdot H_2O$ was dissolved in 750 g of water to prepare a raw material liquid for zeolite. A solution prepared by dissolving 500 g of Cataloid Si-30 liquid glass (manufactured by Catalysts & Chemicals Industries Co, Ltd.) in 333 g of water, 177.5 g of 6% by mass NaOH aqueous solution, 317.6 g of 21.3% by mass aqueous tetrapropylammonium bromide solution, and 15.0 g (corresponding to 10% by mass of the amount of a zeolite catalyst synthesized without adding seed crystals) of an ammonium-type, MFI-type zeolite (manufactured by Zeolyst International, Si/Al atomic ratio: 70) having an average particle size of 0.5 μm as zeolite seed crystals were added to the raw material liquid while stirring to obtain an aqueous gel mixture.

Next, the aqueous gel mixture was placed in a 3-L autoclave, and hydrothermal synthesis was carried out by stirring under self pressure at 160° C. for 18 hours. A white solid product obtained by the hydrothermal synthesis was filtered and washed with water, and then dryed at 120° C. for 5 hours, followed by calcination in air at 520° C. for 10 hours. The calcined product was immersed in 0.6 N hydrochloric acid, followed by stirring at room temperature for 24 hours to convert the type of zeolite to a proton type.

Then, the product was filtered and washed with water, dried at 120° C. for 5 hours, and calcined in air at 520° C. for 10 hours. Thereby, a proton-type, MFI-type zeolite solid catalyst component containing an alkaline-earth metal component was obtained. In the reactant mixture, atomic ratio Si/Al was 100 and the atomic ratio Ca/Al was 2.5. In the resulting zeolite solid catalyst component, the atomic ratio Si/Al was 100 and the atomic ratio Ca/Al was 3.7. The atomic ratios of the reactant mixture were determined by calculation from the purity and mass of the materials. The atomic ratios after the synthesis were determined by measuring with a fluorescent X-ray analyzer.

The average particle size of the resulting zeolite solid catalyst component was measured by a scanning electron microscope, and the specific surface area was measured by a BET adsorption method. As a result, the catalyst had an average particle size of 1.5 μm and a specific surface area of 320 m²/g.

Boehmite (28 g) was mixed with 100 g of the resulting zeolite solid catalyst component in the form of powder, and kneading was performed using an appropriate amount of ion-exchange water. The resulting mixture was formed into columnar pellets with a diameter(D) of 1.8 mm and an average length (L) of 4.2 mm, using an extruder.

Next, the shaped body obtained by the extrusion molding was dried at 120° C., followed by calcination in air at 550° C. for 12 hours. Thereby, catalyst A was obtained. The resulting catalyst A maintained the shape formed by the extrusion molding, and had a thickness of 1.8 mm.

Comparative Example 1

Production of Catalyst B

Catalyst B was produced as in Example 1 except that, in the extrusion molding, columnar pellets with a diameter of 3.6 mm and an average length of 5.9 mm were formed. The resulting catalyst B maintained the shape formed by the extrusion molding, and had a thickness of 3.6 mm.

Comparative Example 2

Production of Catalyst C

Catalyst C was produced as in Example 1 except that, in the extrusion molding, columnar pellets with a diameter of 5.0 mm and an average length of 5.4 mm were formed. The resulting catalyst C maintained the shape formed by the extrusion molding, and had a thickness of 5.0 mm.

Example 2

Production of Catalyst D

Catalyst D was produced as in Example 1 except that, in the extrusion molding, ring-shaped pellets with an outer diameter of 5.0 mm, an inner diameter of 2.0 mm, and an average length of 7.8 mm were formed. The resulting catalyst D maintained the shape formed by the extrusion molding, and had a thickness of 1.5 mm.

Example 3

Production of Catalyst E

The catalyst C obtained in Comparative Example 2 was pulverized by a mortar and passed through a sieve with an opening of 0.50 to 0.59 mm. Thereby, catalyst E with a thickness of 0.59 mm or less was produced.

Example 4

Production of Catalyst F

Figure 2:
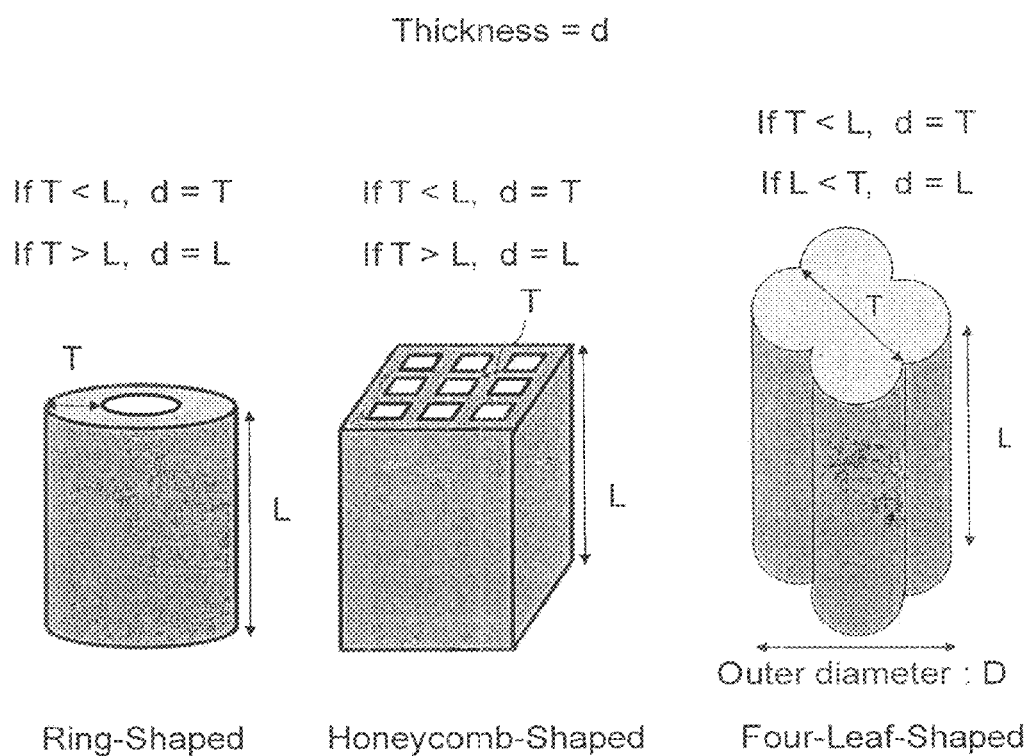
FIG. 2 is a schematic diagram illustrating the thickness of the catalyst in the case where the catalyst shape is ring-shaped, honeycomb-shaped, and four-leaf-shaped in cross-section.

Catalyst F was produced as in Example 1 except that, in the extrusion molding, a 75-mm square honeycomb-shape with a thickness of 1.3 mm as defined by FIG. 2 and a cell diameter of 1.0 mm square was formed. The resulting catalyst F maintained the shape formed by the extrusion molding, and had a thickness of 1.3 mm.

Example 5

Production of Catalyst G

A zeolite solid catalyst component (100 g) obtained as in Example 1 and 28 g of boehmite were mixed, and kneading was performed using an appropriate amount of ion-exchange water to obtain a mixture. The resulting mixture was applied by coating onto 106 g of a honeycomb-shaped silica carrier with a thickness of 0.2 mm, a cell diameter of 2.0 mm, and an average length of 24.0 mm, and drying and calcining were performed as in Example 1. Thereby, honeycomb-shaped catalyst G with a thickness of 0.3 mm was obtained.

Example 5b

Production of Catalyst H

Catalyst H was produced as in Example 1 except that, in the extrusion molding, four-leaf-shaped pellets with a length of 7.7 mm, outer diameter of 1.8 mm and T (refer to FIG. 2) of 1.1 mm were formed. The resulting catalyst H maintained the shape formed by the extrusion molding, and had a thickness of 1.1 mm.

Example 6

Production of Lower Olefins

A mixed gas including a mixture of methanol (0.9 NL/min), dimethyl ether (1.9 NL/min), and water vapor (1.9 NL/min) and nitrogen (11.1 NL/min) serving as a dilution gas was continuously supplied to a fixed-bed flow reactor into which catalyst A obtained in Example 1 had been packed, and lower olefins production reaction was carried out. The characteristics (catalyst thickness, CBD, catalyst shape, and catalyst diameter) of the catalyst used and the catalyst packing density in the reactor are shown in Table 1.

The reaction conditions were set as follows: WHSV (DME): 1.0 h$^{-1}$, reaction pressure: 0.5 MPa, and inlet temperature: 400° C. The weight hourly space velocity (WHSV (DME)) was the weight of the supplied reactant (total of dimethyl ether and methanol) in terms of dimethyl ether (g-DME), per unit time (h), and per unit weight of catalyst (g-cat). The unit of measure of WHSV is h$^{-1}$.

The reaction was continuously carried out under the conditions described above, the outlet temperature was 560° C. The propylene yield 10 hours after the start of reaction, at which time the reaction was stabilized, was measured by gas chromatography. The results are shown in Table 1.

Furthermore, the reaction was continuously carried out under the conditions described above, and the composition of the reactor exit gas was analyzed and the feedstock conversion was determined. On the basis of this result, the catalyst life was determined.

When the feedstock conversion in terms of dimethyl ether determined from the exit gas composition was 99.9% or lower, the integral amount of dimethyl ether that had been supplied per 1 g of the catalyst was employed to define the relative catalyst life used herein. The catalyst life of example 6 is considered as 100.

Comparative Example 3

Lower olefins were produced as in Example 6 except that catalyst B obtained in Comparative Example 1 was used instead of catalyst A. The results are shown in Table 1.

Comparative Example 4

Lower olefins were produced as in Example 6 except that catalyst C obtained in Comparative Example 2 was used instead of catalyst A. The results are shown in Table 1.

Example 7

Lower olefins were produced as in Example 6 except that catalyst D obtained in Example 2 was used instead of catalyst A.

The results are shown in Table 1.

Example 8

A mixed gas including dimethyl ether (20 Ncc/min) and nitrogen (20 Ncc/min) serving as a dilution gas was continuously supplied to a fixed-bed flow reactor into which catalyst E obtained in Example 3 had been packed, and lower olefins production reaction was carried out. The characteristics (catalyst thickness, CBD, catalyst shape, and catalyst diameter) of the catalyst used and the catalyst packing density in the reactor are shown in Table 1.

The reaction conditions were set as follows: WHSV (DME): 10 h$^{-1}$, inlet pressure: 0 MPa, and catalyst layer temperature: 530° C.

Figure 3:
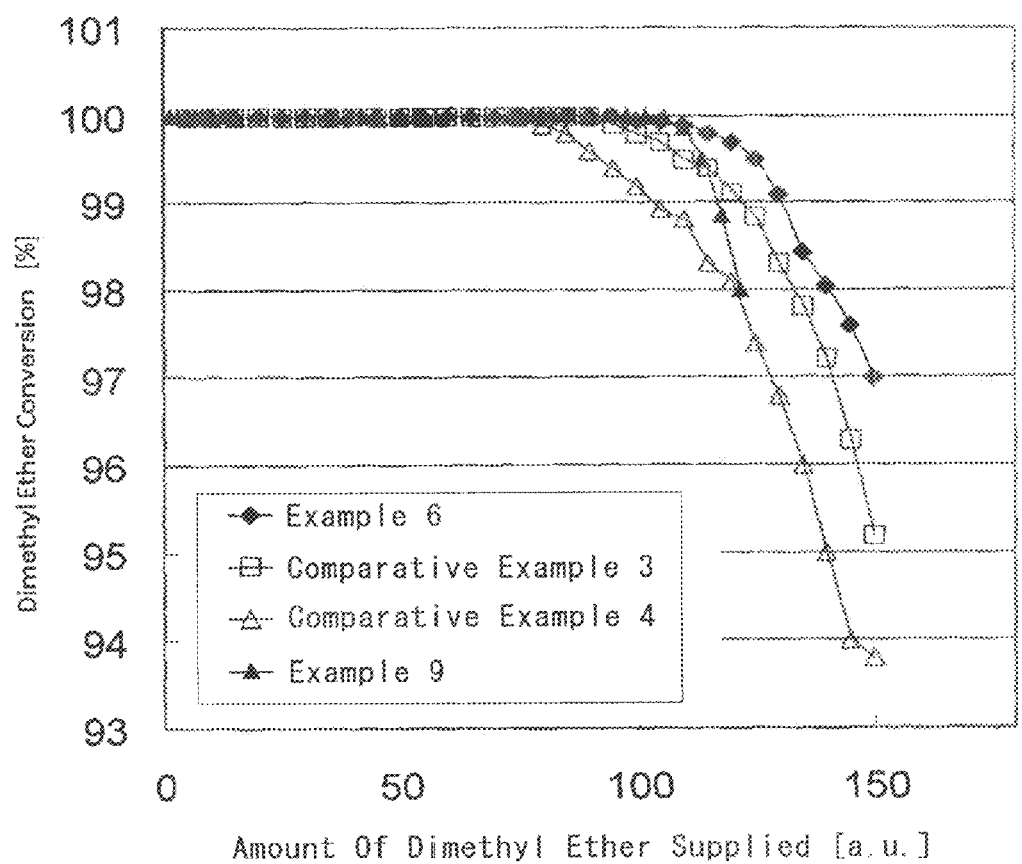
FIG. 3 is a graph showing the time course of the feedstock conversion over catalysts A, B, C, and F obtained in examples and comparative examples.

Furthermore, FIG. 3 is a graph in which the vertical axis represents the dimethyl ether conversion and the horizontal axis represents the amount of dimethyl ether supplied per 1 g of the catalyst when the catalyst life of catalyst A is considered as 100, the graph showing the time course of the feedstock conversion over catalyst A (Example 6), B (Comparative Example 3), C (Comparative Example 4), and F (Example 9).

TABLE 1

| Catalyst | Ex. 6 A | Co-Ex. 3 B | Co-Ex. 4 C | Ex. 7 D | Ex. 8 E | Ex. 9 F | Ex. 10 G | Exa. 11 F | Ex. 12 H |
|---|---|---|---|---|---|---|---|---|---|
| Catalyst thickness (mm) | 1.8 | 3.6 | 5 | 1.5 | <0.59 | 1.3 | 0.3 | 1.3 | 1.1 |
| Catalyst packing density (kg/m$^3$) | 701 | 688 | 669 | 517 | 770 | 544 | 497 | 544 | 610 |
| CBD (kg/m$^3$) | 729 | 712 | 674 | 566 | 800 | 544 | 497 | 544 | 650 |
| Catalyst shape | Columnar | Columnar | Columnar | Ring-shaped | — | Honeycomb | Honeycomb | Honeycomb | Four-leaf-shaped |
| Catalyst diameter (mm) | 1.8 | 3.6 | 5 | Outer 5.0 Inner 2.0 | 0.5 to 0.59 | — | — | — | 1.8 |
| Relative catalyst | 100 | 92 | 80 | 102 | 101 | 98 | 99 | 155 | 102 |
| Propylene yield (wt %) | 36 | 36 | 36 | 37 | 38 | 37 | 38 | 44 | 39 |

The reaction was continuously carried out under the conditions described above, and the catalyst life and the propylene yield were determined as in Example 6. The results are shown in Table 1.

Example 9

Lower olefins were produced as in Example 6 except that, instead of catalyst A, catalyst F obtained in Example 4 was used by cutting to a size that allows the catalyst to be packed in the reactor tube. The results are shown in Table 1.

Example 10

Lower olefins were produced as in Example 6 except that catalyst G obtained in Example 5 was used instead of catalyst A. The results are shown in Table 1.

Example 11

Lower olefins were produced as in Example 9 except that the inlet pressure was set at 0.3 MPa. The reaction was continuously carried out under the conditions described above, the outlet temperature was 560° C. The results are shown in Table 1.

Example 12

Lower olefins were produced as in Example 6 except that catalyst H obtained in Example 5b was used instead of catalyst A. The results are shown in Table 1.

In Table 1, the relative catalyst life in each of Comparative Examples 3 and 4 and Examples 7 to 11 is a relative value in the case where the catalyst life in Example 6 is considered as 100.

As is evident from the results of Examples and Comparative Examples, although good catalyst life is obtained when the thickness of a catalyst is 2.0 mm or less, catalyst life tends to decrease with the thickness of the catalyst when the thickness exceeds 2.0 mm; by decreasing the thickness of a thick catalyst to 2.0 mm or less by pulverization or the like, catalyst life equivalent to a thin catalyst can be obtained; although the thickness of a catalyst greatly affects catalyst life, the influence on the properties of the product is small; and although the influence of the physical shape of a catalyst, such as columnar pellet type, ring-shaped pellet type, or honeycomb type, on the performance of the catalyst is small, the influence of the size or thickness of the catalyst is large.

INDUSTRIAL APPLICABILITY

By use of a lower olefin producing catalyst and a method for producing lower olefins according to the present invention, it is possible to provide a catalyst which is used in producing lower olefins, such as propylene, from an oxygen-containing compound, such as dimethyl ether or methanol, and which has long catalyst life, and a method for producing lower olefins efficiently and economically.

The invention claimed is:
1. A lower olefin producing catalyst comprising:
  a solid-state catalyst component comprising an MFI-type zeolite, the thickness of the catalyst being in a range of from 0.1 to 2.0 mm, where the thickness is defined as a distance twice the shortest distance from the outer surface to a position where the shortest distance to the outer surface is maximum among all positions inside a structure of the solid catalyst, and the compacted bulk density (CBD) of the catalyst being 800 kg/m$^3$ or less,
  wherein the lower olefin producing catalyst is of a shape selected from the group consisting of honeycomb-shaped, three-leaf-shaped and four-leaf-shaped, the solid-state catalyst component contains an alkaline-earth metal component in an amount of 0.3 to 10 parts by weight in terms of metal relative to 100 parts by weight of the MFI-type zeolite.

2. The lower olefin producing catalyst according to claim 1, wherein the lower olefin producing catalyst is obtained by a process comprising shaping a mixture comprising the solid-state catalyst component comprising an MFI-type zeolite, and at least one binder selected from the group consisting of an oxide of aluminum, a hydroxide of aluminum, an oxide of silicon, a hydroxide of silicon and clay.

3. The lower olefin producing catalyst according to claim 2, wherein the alkaline-earth metal is calcium.

4. The lower olefin producing catalyst according to claim 1, wherein the lower olefin producing catalyst is honeycomb-shaped.

5. The lower olefin producing catalyst according to claim 1, wherein the atomic ratio Si/Al in the zeolite framework of the MFI-type zeolite is in a range of from 10 to 2,000.

6. A method for producing a lower olefin producing catalyst comprising:
preparing a mixture by mixing/kneading a solid-state catalyst component comprising an MFI-type zeolite and at least one binder selected from the group consisting of an oxide of aluminum, a hydroxide of aluminum, an oxide of silicon, a hydroxide of silicon, and clay in the presence of a polar solvent; and
shaping the mixture and calcining the shaped mixture,
to obtain the catalyst having a thickness in a range of from 0.1 to 2.0 mm, where the thickness is defined as a distance twice the shortest distance from the outer surface to a position where the shortest distance to the outer surface is maximum among all positions inside a structure of the solid catalyst, and the catalyst having the compacted bulk density (CBD) of 800 kg/m$^3$ or less,
wherein the lower olefin producing catalyst is of a shape selected from the group consisting of honeycomb-shaped, three-leaf-shaped and four-leaf-shaped, the solid-state catalyst component contains an alkaline-earth metal component in an amount of 0.3 to 10 parts by weight in terms of metal relative to 100 parts by weight of the MFI-type zeolite.

7. A method for producing lower olefins comprising:
contacting an oxygen-containing compound with the lower olefin producing catalyst according to claim 1 in a reactor into which the catalyst has been packed at 500° C. to 650° C. of outlet temperature under 0.12 MPa to 1.0 MPa of inlet pressure.

8. The method for producing lower olefins according to claim 7, wherein the oxygen-containing compound comprises dimethyl ether and/or methanol.

9. The method for producing lower olefins according to claim 7, wherein the catalyst packing density in the reactor is 800 kg/m$^3$ or less.

10. The method for producing lower olefins according to claim 8, wherein the catalyst packing density in the reactor is 800 kg/m$^3$ or less.

11. The lower olefin producing catalyst according to claim 1, wherein the alkaline-earth metal is calcium.

12. The lower olefin producing catalyst according to claim 1, wherein the atomic ratio Si/Al in the zeolite framework of the MFI-type zeolite is in a range of 50 to 1,000.

13. The lower olefin producing catalyst according to claim 1, wherein the compacted bulk density (CBD) of the catalyst is 729 kg/m$^3$ or less.

14. The lower olefin producing catalyst according to claim 1, wherein the compacted bulk density (CBD) of the catalyst is 700 kg/m$^3$ or less.

15. The lower olefin producing catalyst according to claim 1, wherein the compacted bulk density (CBD) of the catalyst is 650 kg/m$^3$ or less.

16. The lower olefin producing catalyst according to claim 1, wherein the compacted bulk density (CBD) of the catalyst ranges from 200 to 650 kg/m$^3$.

* * * * *